(12) United States Patent
Azenkot

(10) Patent No.: US 12,140,583 B2
(45) Date of Patent: Nov. 12, 2024

(54) LYSIMETER DEVICE

(71) Applicant: Asher Azenkot, Ramat Yishi (IL)

(72) Inventor: Asher Azenkot, Ramat Yishi (IL)

( * ) Notice: Subject to any disclaimer, the term of this patent is extended or adjusted under 35 U.S.C. 154(b) by 306 days.

(21) Appl. No.: 17/767,967

(22) PCT Filed: Jun. 2, 2021

(86) PCT No.: PCT/IL2021/050652
§ 371 (c)(1),
(2) Date: Apr. 11, 2022

(87) PCT Pub. No.: WO2022/043982
PCT Pub. Date: Mar. 3, 2022

(65) Prior Publication Data
US 2023/0280328 A1    Sep. 7, 2023

Related U.S. Application Data

(60) Provisional application No. 63/072,208, filed on Aug. 30, 2020.

(51) Int. Cl.
*G01N 33/24* (2006.01)
*G01N 1/14* (2006.01)

(52) U.S. Cl.
CPC .............. *G01N 33/24* (2013.01); *G01N 1/14* (2013.01); *G01N 33/245* (2024.05)

(58) Field of Classification Search
CPC ................ G01N 33/24; G01N 33/246; G01N 2033/243; G01N 2033/245; A01B 79/005
See application file for complete search history.

(56) References Cited

U.S. PATENT DOCUMENTS

| 4,759,227 A * | 7/1988 | Timmons | ................ E02D 1/06 73/864.34 |
| 2003/0121336 A1* | 7/2003 | Hubbell | ................ E02D 1/06 73/863.23 |

* cited by examiner

*Primary Examiner* — Benjamin R Schmitt
(74) *Attorney, Agent, or Firm* — The Roy Gross Law Firm, LLC; Roy Gross

(57) ABSTRACT

A lysimeter device used for monitoring and measuring the concentration of water soluble compounds in the soil without disturbing the natural flow pattern of water in the soil and constructed of two tubes, the first tube inserted into the second tube, a sealing plate and a clogging prevention component (CPC). A lysimeter device for monitoring the concentration of soluble fertilizer' compounds, total salinity and pesticides commonly used in agriculture and gardening and their uptake by plants while not disturbing the plants roots soil environment and with no need for an external power/energy source for functioning.

20 Claims, 3 Drawing Sheets

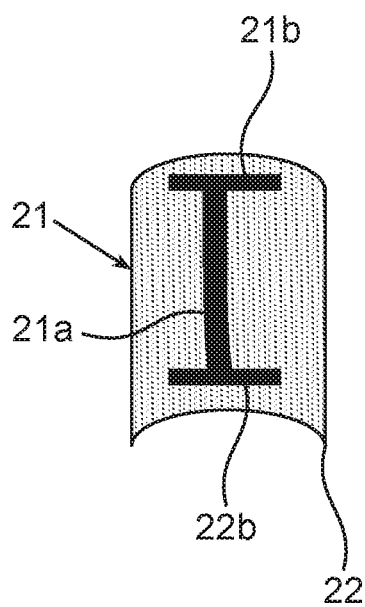
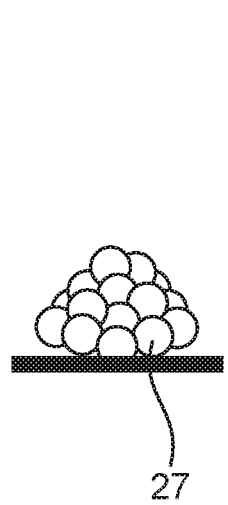
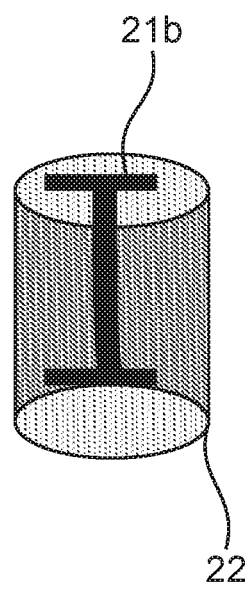
Fig. 3a
Fig. 3b
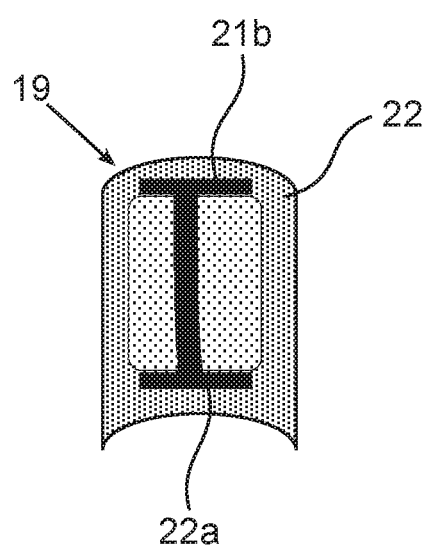
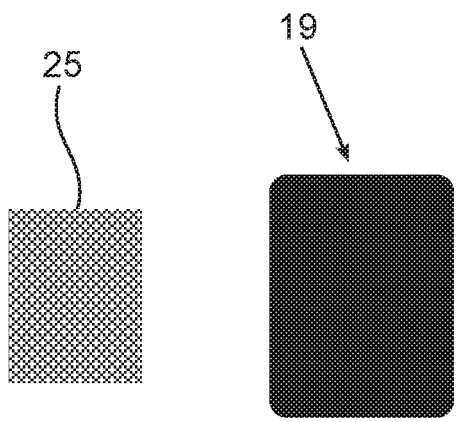
Fig. 3c
Fig. 3d

LYSIMETER DEVICE

FIELD OF THE INVENTION

The present invention relates to a lysimeter device. The lysimeter device of the invention has a preferred configuration that is compact and small size and is referred to in the text as "a micro-lysimeter". The lysimeter of the invention is a device for monitoring the concentration of water soluble compounds in the soil without disturbing the natural flow pattern of water in the soil. More specifically, the present invention relates to monitoring the concentration of soluble fertilizer' compounds, total salinity and pesticides commonly used in agriculture and gardening and their uptake by plants while not disturbing the plants roots soil environment and with no need for an external power/energy source for functioning.

BACKGROUND OF THE INVENTION

The term "lysimeter" is derived from the Greek work meaning "loosening" with the suffix-meter. Lysimeters are devices typically used in agriculture for measuring and monitoring the transmission rate of water soluble compounds in the soil. The term "compounds" in the present text refers to chemical substances required by plants for growth (compounds found in plant fertilizers and naturally in the soil) as well as to soil-salinity mineral substances and pesticides.

When water containing water soluble fertilizing compounds such as nitrates, phosphates and various other compounds required by plants are spread in a field (by any type of irrigation such as, drip irrigation, spraying or center pivot irrigation system, it is of major interest, both economically and environmentally, that the compounds of the fertilizers be absorbed by the plants roots and do not run-off from the reach of the plants, causing environmental pollution. Of major concern is the leaching to the environment of excess nitrates.

Another category of water soluble compounds that are spread in agricultural fields are herbicides, insecticides and fungicides, referred to in the present text as "pesticides". As was described for fertilizers, when excess water soluble pesticides are applied into the soil so as to overshoot the desirable/acceptable soil concentration, the run-off of the pesticides from the reach of the plants may cause undesired results, both economically and environmentally. In the present text, references made to water soluble compounds of fertilizers also refers to water soluble pesticides.

The calculation of the concentration of the fertilizing compounds applied and entering into the soil with a given volume of water per unit area and measuring the concentration of the fertilizing compounds in the relevant soil-volume beneath the roots of the plants in the field per the same unit area, enables to calculate the efficiency of the uptake of the fertilizing compounds by the plants, thus, enabling the optimization of the concentrations of the fertilizing compounds to be applied in the following irrigation-water for preventing over-fertilization.

When fields are irrigated by rain there is no exact determination of the amount of water that is/was applied to a given area per given time. Yet, with rain irrigation the issue of preventing the input of excess fertilizing compounds to a given area remains the same as described previously for human-operated field irrigation systems. In the case of rain, fertilizing compounds are applied to the soil in a liquid or solid form and the rain-water "drive" the compounds into/through the soil. The efficiency of the uptake of the fertilizing compounds by the plants can be determined by calculating the concentration of the compounds spread over a given area and measuring the concentration of the compounds in the soil beneath the roots of the plants in the same given area.

The science of soil analysis includes measurements of the soil's nutrients-holding capacity as well as the present soil's nutrient concentrations and provides a basis for agriculture management decisions related to certain defined area or plot. Soil analysis may include the measurement of the concentrations of various nitrogen and phosphorus containing compounds as well as other nutrients and the pH of the soil. Soil analysis measurements also enable monitoring the use of various pesticides. Soil nutrient concentrations in each measurement-location vary along the vertical depth column/core of the soil and vary over time. The difficulty of routinely performing soil analysis in samples beneath the roots of plants is obtaining such samples without obtaining contaminants from the surrounding soil and not disturbing the natural flow pattern of the water through the soil so as to obtain a true representative sample. Another aspect that has to be considered is the significant length of time (several days up to two weeks) to complete soil analysis done in laboratories. When received, the laboratory obtained results may no longer be relevant.

An alternative to soil analysis is the analysis of the dissolved mineral compounds content of water extracted from the soil, referred to as "soil water", beneath the roots of plants. Water content analysis are much easier and less expensive to preform them soil analysis. The idea of using a lysimeter devices for collecting water samples beneath the roots of plants in the field for chemical analysis is not new. Two examples of such devices are described in RU2619554 (Golubenk): Lysimetere device and U.S. Pat. No. 8,763,478 (Riess and Crass): Environmental sampler and method of using same. The problems with the currently disclosed lysiometer devices are: 1) the technique of insertion of the devices beneath the roots of plants hinders the structure of the soil layers, thus, distorting the flow pattern of the water and the composition of the dissolved concentration of the compounds found in the water that represent the concentration of the compounds found in the soil under the roots. 2) the clogging of the entrance of the water into the lysimeter device by the soil surrounding the device. 3) a power (energy) source is often required to operate the device.

The present invention relates to a lysimeter device, having, a preferred embodiment that is, but not limited to, compact, small size tube. A small size, compact configuration of the device is referred in the text that follows interchangeably as a "micro-lysimeter device". The lysimeter of the invention has a spatial configuration of a tube that, when deployed, is inserted into the soil between and/or beneath the roots of plants of interest. The tube configuration, of the lysimeter enables the flow of water in the soil while minimizing the hindrance to the course of the water flow in the soil. The narrower the size of the lysimeter's tube, the less hindrance is caused to the flow patterns of the water in the soil. A clogging prevention component (CPC), its structure is explained later in the text, prevents the clogging of the entrance to the lysimeter by particles and insects from the surrounding soil while enabling the free passage of water into (and out of) the device. The lysimeter device enables monitoring the concentration of mineral compounds in the soil after every irrigation cycle or rainfall by the use of (but not limited to) a hand operated home water analysis kit or/and more sophisticated laboratory chemical analysis means. Optionally, online sensors that transmit the results to a receiving and recording device, or in a laboratory can be deployed in the lysimeter. In the present invention the analysis is done on a sample of soil water instead of directly in the soil, which significantly reduces the time and labor required for the analysis. The term "soil water" is used in the text refers to water that contain dissolved compounds from the soil of which the water flowed through

SUMMARY OF THE INVENTION

The present invention relates to a lysimeter device. A preferred configuration embodiment of the lysimeter device is a compact, small size, lysimetric device of the invention. The small size, compact configuration of the device (to be described later in the text) is referred in the text as a "micro-lysimeter device".

The lysimeter device of the invention is constructed of an external tube made of a hard, inert material such as, but not limited to, plastic or metal, having a different length, depending on the depth desired in the soil. The end of the tube that is inserted into the ground, referred to in the text as the "bottom side of the tube", is sealed by a sealing plate. A flexible tube (referred to interchangeably as the "internal tube"), which has substantially smaller external and inner diameters relatively to the external tube, is inserted into the external tube so as to almost reach, but not touch, the sealing plate. The internal tube extends from the external tube from the free/open side of the tube. Typically, but not limited to, the flexible tube is made of a plastic material. Optionally, the sealing plate has in it at least one open-hole (See FIG. 1).

The external tube has an opening in the wall of the tube in the portion of the tube in the near of the sealing plate. The opening is a hole in the wall but can, optionally also be several holes or a proliferated surface.

The opening in the wall of the external tube is covered by a fixated clogging-prevention-component (CPC) which is composed of: a geotechnical textile fabric component, a stabilizing-bar component and inert material beads.

The geotechnical textile fabrics is typically a non-woven fabric, synthetic fiber gauze, or any material or membrane that allows liquids to pass through it and can withstand the exposure to soil environment for long time periods (of many years). The inert material beads are typically made of glass or any other hard and chemically inert material. In forming the CPC, the geotechnical textile fully encapsulates the beads by at least one layer. The CPC is placed so as to completely cover opening(s) hole of the external tube and is fixated in place by, but not limited to, water resistant glue or tape. The combination of the beads and the geotechnical textile enables the infiltration of the water into (and out of) the lysimeter device without letting soil particles and other undesired elements such as insects or worms to enter the tube. The combination of the beads and the geotechnical textile at the water entrance(s) to the device form a delicate structural configuration that is exposed to physical damage during the insertion and removal of the lysimeter into and out of the soil. In order to protect the CPC structure, optionally, a protection net is optionally placed over the structure to prevent physical damage by abrasion and tearing.

When the lysimeter is deployed, the bottom side of the device is inserted into the soil. If no excess water is to be found in the soil (the soil is not being saturated) no water will flow into the tube. Between irrigation cycles (agricultural/gardening input water) or rain fall, the water is typically held by soil with a negative force of $-0.33$ atmospheres or less. Thus, the lysimeter cannot collect in-flowing water until water is added to the soil in the following irrigation or rain fall cycle. When the top of the soil is wetted and water-saturated, the excess water forms a saturated-soil front that penetrates into the depth of the soil. As the front advances into the soil, the excess water that is not held ("captured") by the wetted (saturated) soil continues its way downwards. On its way into the soil the excess water flows into the external tube of the lyismeter of the invention, through the opening in a drainage manner. The water entering the lysimeter will fill the tube with water that has passed through the roots of the plants above and have dissolved the available agricultural-used compounds found in the soil. As the front of the water advances into the soil and no additional water is added from the top soil (before the soil being irrigated again) the soil gradually dries. When the soil is no longer water saturated, the water above the lower rim of the lysimetric will gradually exit the lysimeter into the surrounding soil. The water that is below the lower rim of the opening of the external tube will be blocked and not be able to exit external tube, thus, will remain "trapped" in the tube. The "trapped" water will be sampled for the water soluble compounds in the soil.

The available dissolved compounds are the agricultural used compounds not taken up by the roots of the plants at the time of the soil water analysis, thus, found in excess, and are "washed away" with the water penetrating the soil.

The lysimeter device (preferably in a mico-lysimeter configuration) is inserted and installed in the soil typically at an angle of approximately 45° relative to the surface of soil, as shown in FIG. 4. Since the lysimeter has a relatively small diameter and is not perpendicular to the surface, it does not interfere in any meaning way with the water flow and the soil's water solution quality remains unaffected. As long as the upper-side end of the external tube of the device remains above the surface of the soil, the lysimeter can be placed anywhere in the soil profile, within the root system or under the root system. Being in close vicinity of the roots, the water collected by the device reflects the concentration of compounds the soil contains in the near of the roots. As the size of the tube of the lysimeter is increased, hindrance in the soil increases.

The water and compounds flow in the soil during every wetting cycle done by rain fall or human water soil-input. Rain fall and/or agricultural/gardening input of water is referred to in the text as "irrigation". The soil water dissolved mineral compounds interact with soil particles and plants root system. While the water flows into the soil, it also flows into the lysimeter through the opening(s) using gravity. The soil water that flows into the lysimeter is representative of the soil water nearby. The collected water in the external tube is sucked out of the lysimeter through the flexible inner tube from the bottom end of the external tube (typically, using a syringe of a pump) and the concentration of the dissolved mineral compounds of interest be analyzed. The analysis can be made using analytical methods deployed in standard water or in a more sophisticated analytical laboratory. In deploying the lysimeter (in collecting the water from the soil) no external power/energy source is required for the entry of water into the device.

Optionally, a sensors (or sensors) for soluble soil compounds analysis is inserted into the collected soil water inside the external tube of the lysimeter and detects and measures the concentration of the desired chemical compound of interest. The collected data from the sensor(s) is transmitted by wire or by a wireless transmission to a receiving and recording device for automated analysis device. Analysis data can be read in the field from on-site analysis devices and via hand held receiving devices, or transmitted via wires or wirelessly to the cloud for real-time analysis and recording, thus, becoming available to those granted access to the information from any Internet connection or smart phone device.

BRIEF DESCRIPTION OF THE DRAWINGS

In order to better understand the present invention, and appreciate its practical applications, the following figures are provided and referenced hereafter. It should be noted that the figures are given as examples only and in no way limit the scope of the invention. Like components are denoted by like reference numerals.

FIG. 3a is an illustration of the components of the clogging prevention component (CPC) of the lysimeter device shown in FIG. 1: a geotechnical fabric textile component, a stabilizing component and glass beads.

FIG. 3b is an illustration of the CPC shown in FIG. 2a, showing the geotechnical fabric textile component (in a transparent configuration) wrapped around the stabilizing component with it bottom portion in a sealed configuration.

FIG. 3c is a crosscut illustration of the CPC of the lysimeter shown device in FIG. 2b, showing the geotechnical fabric component wrapped around the stabilizing component and the glass beads tightly packed between the geotechnical fabric textile component and the stabilizing component.

FIG. 3d is an isometric illustration of CPC as connected to the lysimeter device shown in FIG. 1, in an assembled configuration with an optional protective net positioned beside it.

DETAILED DESCRIPTION OF PREFERRED EMBODIMENT

The present invention relates to a lysimeter device. A preferred embodiment of the invention is a small size, compact lysimetric device, referred in the text that follows as a "micro-lysimeter device". The term "lysimeter device" and "micro-lysimeter device" are used interchangeably in describing the structure and use of the lysimter device of the invention. In describing the structure of the embodiment of the invention, the provided dimensions constitute the structure of a micro-lysimeter devices.

Figure 1:
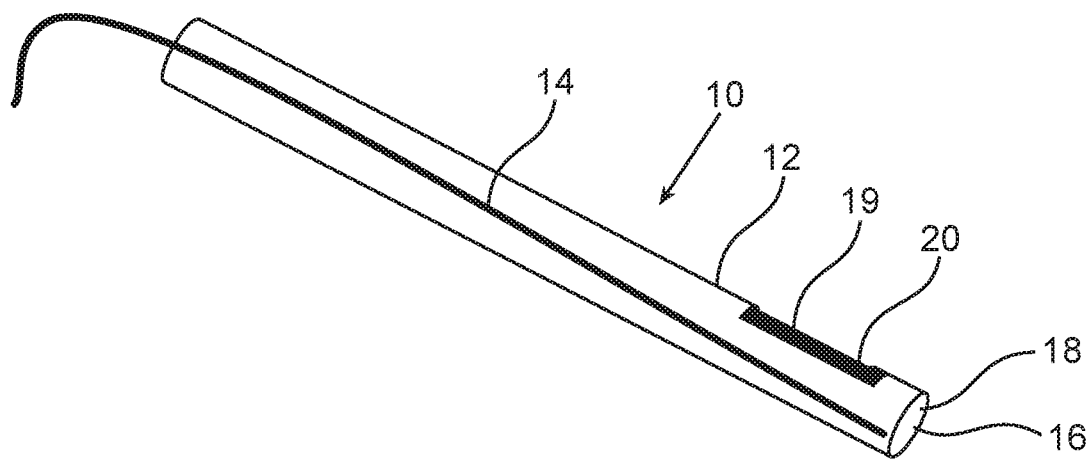
FIG. 1 is an isometric illustration of a lysimeter device viewed from the side with the external tube shown in a transparent configuration to enable viewing the internal tube.
Figure 2:
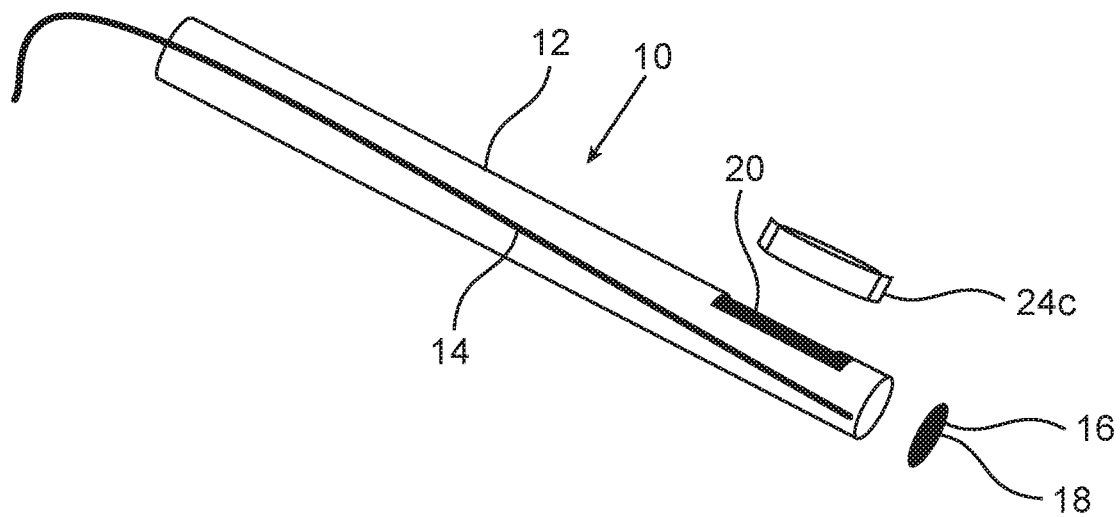
FIG. 2 is the lysimeter device shown in FIG. 1 in a disassembled configuration

FIG. 1 is an isometric illustration of a lysimeter device (10) of the invention viewed from the side. FIG. 2 is the lysimeter device (10) shown in FIG. 1 in a disassembled configuration Device (10) is constructed of an external tube (12) made of a hard, inert material such as, but not limited to, plastic or metal having an external diameter of, but not limited to, between 4 and 6.3 cm and an internal diameter of, but not limited to, between 3.6 and 5.7 cm. In the figure, tube (12) is shown in a transparent configuration to enable the view of the internal construction of device (10). Typical the length of the external tube is, but not limited to, 50 to 150 cm. The length of tube (12) can vary substantially, depending on the depth of which lysimeter is meant to be inserted into the soil and soil water samples be analyzed. The bottom side of tube (12) (the side being inserted into the soil) is closed by a sealing plate (16). Optionally, sealing plate (16) has at least one hole-opening in it (18), typically but not limited to, 0.5 cm in diameter. A flexible, internal tube (14), substantially smaller in its outer and inner diameter then the external tube, is inserted into external tube (12) and runs all the way through tube, but not touching, sealing plate (16). Typically, but not limited to, internal tube (14) is made of a plastic material and has, but not limited to, dimensions of between 0.5 and 1.0 external diameters and between 0.3 and 0.7 cm inner diameters. Typically, the distance of the end of internal tube (14) and sealing plate (16) is, but not limited to, between 1.0 and 2.0 cm External tube (12) has an open-hole (20), located towards the bottom portion of the tube, but not reaching sealing plate (16). The distance between sealing plate (16) and bottom-side rim of the open-hole is, but not limited to, between 12 and 20 cm. Typically the shape of the open-hole is a longitudinal cut in external tube (12) having a longitudinal dimension of, but not limited to, between 10 and 25 cm and a width of, but not limited to, between 2 and 8 cm. Optionally, instead of a single open-hole (20), the opening in external tube (12) is a perforated area having more then a single hole. A clogging prevention component, referred to as CPC (19), is fixated at entrance to open-hole(s) (20).

The structure of the CPC is explained in FIGS. 3a to 3d and in the text that follows:

Shown in FIG. 3a are the three components of which the clogging prevention component (CPC) (19) is composed of: a stabilizing-bar component (21) a geotechnical textile fabric component (22), and inert material beads (27). Typically, but not limited to, the length of the CPC (19) is between 0.5 and 1.5 cm longer then the longitudinal length of the open-hole (20) of the external tube (12), illustrated in FIG. 1 and FIG. 2.

Stabilizing-bar component (21) is composed of a bar (21a), typically but not limited to a round tube, made of a hard and inert material such as, but limited to, plastic or metal. If and when stabilizing component bar (21a)) is a tube, typically the external diameter of the tube is, but no limited to, between 0.5 and 3.5 cm. Optionally, the bar (21a) of stabilizing component (21) has on both its edges vertically protruding edge-walls (21b). The height of the edge-walls (21b) above bar (21a) is approximately the combined thickness of the wrapped-around bar (21a) geotechnical fabric textile component (22) together with the inert material beads (24) between the bar (21a) and the fabric (22), shown in FIG. 3c.

The geotechnical textile fabric component (22) is typically made of non-woven cloth, typically produced from polypropylene or polyester and able to endure soil exposure conditions for very long time periods (measured in years). An example of a geotechnical textile fabric is the product: Geoderon® Peit produced by the Edifloor S.P.A. Company of Italy. Geotechnical textile fabrics typically used in the invention have a thickness of 3.5 to 5 millimeters and weight of 400-600 grams per square meter.

The beads (27), shown in FIG. 3a, are composed of an inert material and have a diameter of, but not limited to, between 600 and 1,000 micrometer. Typically, but not limited to, the beads are made of glass or ceramic material.

FIG. 3b is an illustration of CPC (19) shown in FIG. 3a, showing the geotechnical fabric textile component (22) in a transparent view, wrapped around the stabilizing component with its bottom portion in a sealed configuration.

FIG. 3c is a crosscut illustration of the CPC (19) shown device in FIG. 3b, showing the geotechnical fabric component wrapped around the stabilizing component with the glass beads tightly packed between the geotechnical fabric textile component and the stabilizing component.

FIG. 3d is an isometric illustration of the CPC (19) in an assembled configuration that connects to the lysimeter device shown in FIG. 1, with an optional protective net shown positioned beside the CPC.

The combination of the geotechnical textile fabric (22) and the beads (27) form a protective filter that prevent the clogging of the entrance and stops soil particles, debris and insects entering into the external tube (12) of lysimeter device (10), thus preventing the reduction of its efficiency and effectiveness by the reduction of the water-flow intake rate and contamination by undesired elements in the collected water. The CBC (19) also enables an efficient outflow of water from device (10).

Since the geotechnical fabric textile component (22) and beads (27) are liable to be physically damaged when the lysimeter device is inserted into and removed from the soil, optionally a protective net (25) is placed over and layers. Optional protective net (25), illustrated in FIG. 3d, is typically made of, but not limited to, an inert, semi-rigid plastic material, having holes that enable the free passage of water through the net, typically within range of 0.2 to 1 cm in width.

The CPC (19) is constructed by wrapping the geotechnical fabric textile (22) around bar (21a), forming at least one layer, and tightening and closing (only) one edge of the fabric (22) around bar (21a) and leaving the second edge open. Free space is left between the wrapped-around geotechnical fabric textile (22) and the bar (21a). Optionally the tightening and closing is done over and around the protruding edge-wall (21b) of stabilizing bar (21a). After tightening and closing one edge of the wrapped around geotechnical fabric textile (22) the inert beads (27) are poured through the open edge of the wrapped around geotechnical fabric textile (22) into the space between the fabric (22) and the bar (21a)—illustrated in FIGS. 3b and 3c. The inert beads are packed in the space and the open side of the wrapped around geotechnical fabric textile (22) is tightened and closed. Optionally the tightening and closing is done over and around the second protruding edge-wall (21b) as illustrated in FIG. 3d. The CPC (19), with the inert beads (27) encapsulated by the fabric (22), is ready to be fixated together with optional protective net (25) in opening (20) of tube (12) of the lysimeter (10), as illustrated in s FIG. 2. Typically, but not limited to, the fixation of CPC (19) to the opening (20) of the lysimeter (10) is done by water resistant glue or tape.

As shown in FIG. 1, CPC (19) is positioned so as to completely cover opening(s) (20) of tube (12) so as to prevent water from entering external tube (12) without passing through the CPC (19) when the device is deployed. The covering of opening(s) (20) by the CPC (19) is done in a configuration that maintains the smooth outline of external tube (12), so as to enable its insertion into the soil without deforming the covering of the opening(s). Optionally, protective net (25) (not shown in the figure) is fixated in place to completely cover CPC (19). When open hole (20) of tube (12) consists of a configuration of more than one opening, optionally, more than a single CPC (19) is used to cover the openings.

Figure 4:
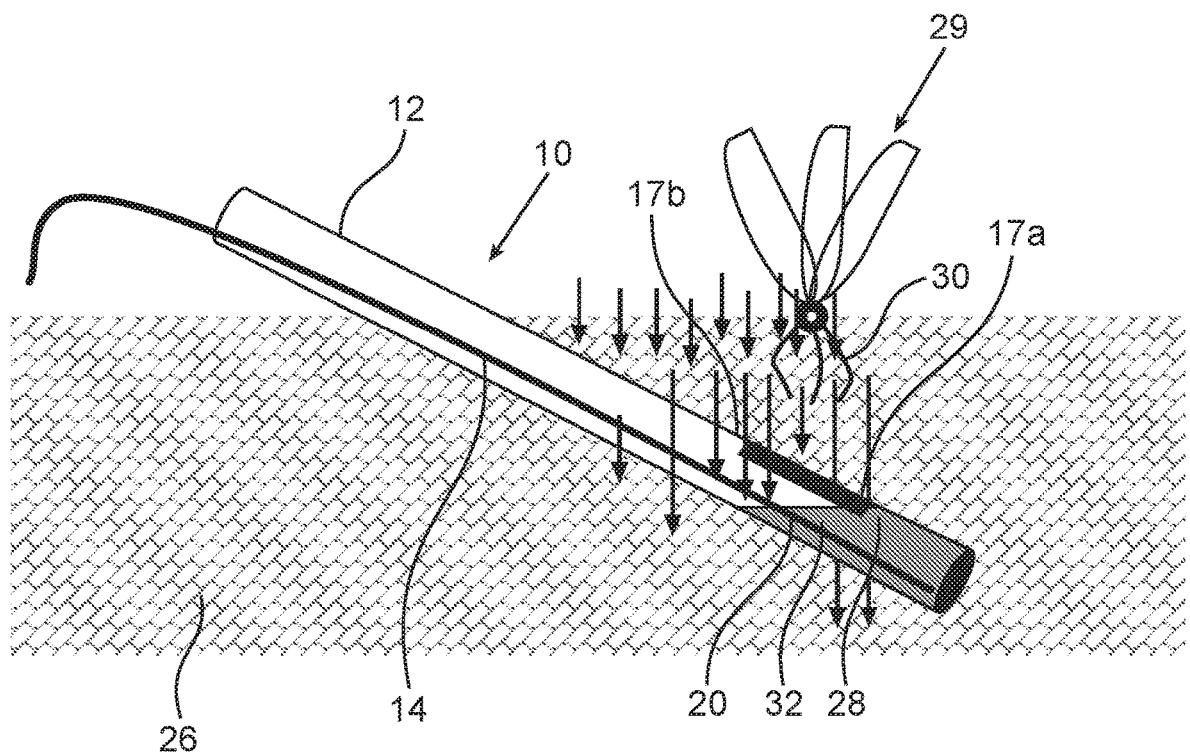
FIG. 4 is an illustration of the lysimeter device of FIG. 1, being deployed by being inserted into the soil under the roots of plants, with water flowing downwards from the top surface of the soil.

FIG. 4 illustrates the lysimeter device (10) shown in of FIG. 1, inserted into the soil (26) at an angle of approximately 45° relative to the surface of the soil with water coming downwards from the top surface of the soil (designated with arrows (28)). The open-hole (20) of lysimeter (10) is shown to be under the roots (30) of the plants (29) planted in the soil (26). Water (28) is shown passing through the soil (26) while passing amongst the roots (30), entering the lysimetric (10) via open-hole (20) and accumulate in tube (12). The water in tube (12) is designated (32).

As was previously explained, water enters tube (12) through open-hole (20) from the soil (26) when the soil is water-saturated after irrigation.

For chemical analysis the water from tube (12), "trapped" under bottom-most-point (17a) is sucked up via internal tube (14). Suction can be done manually or by an electrical pump. The water removed from tube (12) is eventually replaced by water coming from the soil (26) that surrounds device (10) when the soil become again water saturated. For analysis of a water sample it is sufficient that the top layer of the soil of the plot dealt, which contains most of the roots of the plants, is not water saturated after being irrigated. The determination of no-water-saturation is made by gardeners, farmers and/or agricultural professionals that have experience with plant growing. Since the entry and exit of water into and from external tube (12) is done by natural water-streaming phenomena, there is no need for an external power/energy source to keep the lysimeter active.

Figure 5:
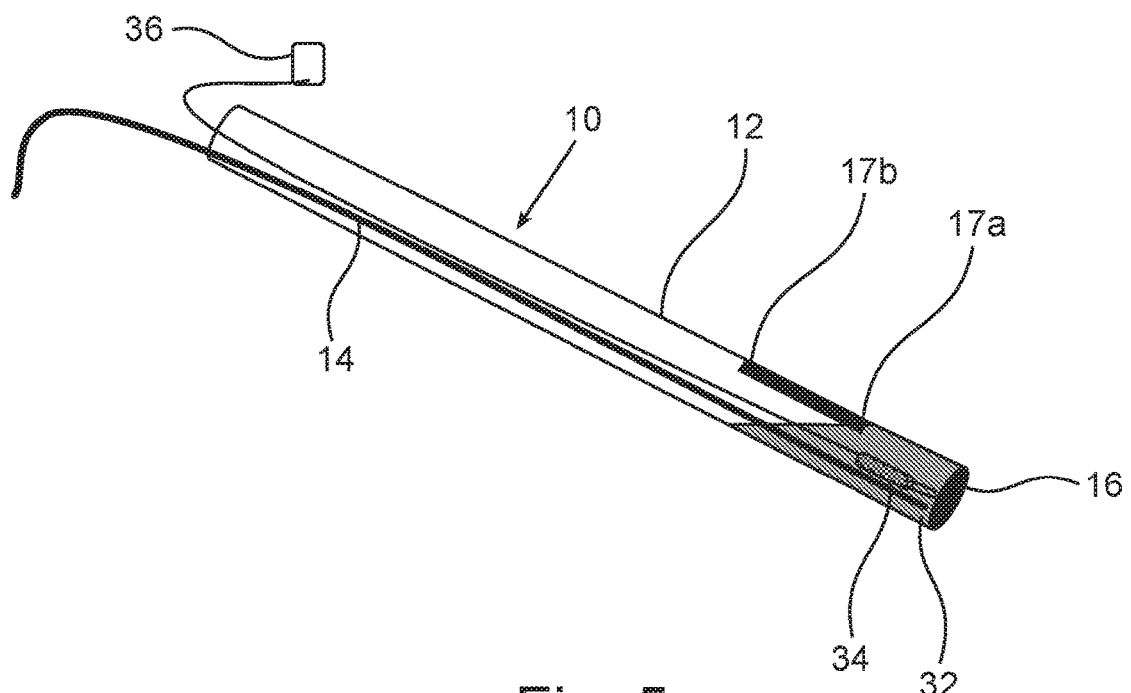
FIG. 5 is an illustration of the lysimeter device of FIG. 1 filled with water and a sensor shown in the external tube.

FIG. 5 illustrates lysimeter device (10) of FIG. 1 with a sensor (or sensors) (34) positioned in the external tube (12) and in the water (32) that fill tube (12). Optionally, at least one type of sensor is used in the embodiment of device (10), shown in FIG. 4. The sensor(s) can be positioned in any location within the volume of water (32) within tube (12) when the-lysimeter device (10) is deployed. Typically, but not limited to, a nitrates detection and recording sensor (34) is deployed for monitoring the effective use of fertilizers containing soluble nitrogen compounds. Other commonly used sensors used in agricultural soil content analysis are used electrical conductivity (indicating salinity concentration) and pH sensors. The recorded data from the sensor(s) is transmitted by wire or a wireless transmition connection (36) to a receiving device such as, but not limited to, a computer data logger or a mobile phone. The collected data is further processed to be useful for immediate and/or future agricultural activities and research.

In FIG. 1, FIG. 2 and FIG. 5, sealing plate (16) of external tube (12) is shown with an optional hole opening (18). Opening hole (18) enables the water entering tube (12) from the surrounding soil to exit external tube (12), disregarding the limitation of the "trapped" water in the volume below lower rim of opening (20) of tube (12), as was previously described. Through opening hole (18) water will pass inside device (10) as part of the water front advancing from the top of the soil downwards. The lysimeter device (10) with opening hole (18) can (only) be used when a sensor (or sensors) are deployed in the device and the reading obtained from the sensor(s) is a continuous measurement of the changing of the soluble soil components.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

I claim:

1. A lysimeter device for monitoring and measuring the concentration of water-soluble compounds in the soil comprising:
   two tubes, the first tube inserted into the second tube,
   a sealing plate,
   a clogging prevention component (CPC),
   the external tube is sealed by said sealing plate at one end of said external tube,
   said external tube has the internal tube inserted into it so as have said internal tube not reaching nor touching said sealing plate,
   said internal tube extends outward from said external tube from the open end of said external tube,
   said external tube has an opening in the wall of said tube in a portion above said sealing plate,
   said opening in said external tube is covered by said CPC and said CPC is fixated to the opening, said CPC comprises:
   a stabilizing-bar component, a geotechnical textile fabric component, and inert material beads,
   said geotechnical textile fabric component is wrapped and engulfs said stabilizing-bar component having said inert material beads packed between said stabilizing bar and said geotechnical textile fabric component.

2. The lysimeter device of claim 1, wherein, said external tube and said sealing plate are made of a hard, inert material.

3. The lysimeter device of claim 2, wherein, said external tube and said sealing plate are made of a plastic material.

4. The lysimeter device of claim 1, wherein, said external tube has a length between 50.0 and 150.0 cm.

5. The lysimeter device of claim 1, wherein, said external tube has an external diameter between 4.0 and 6.3 cm and an internal diameter between 3.6 and 5.7 cm.

6. The lysimeter device of claim 1, wherein, said internal tube is made of a flexible material.

7. The lysimeter device of claim 5, wherein, said external tube is made of a plastic material.

8. The lysimeter device of claim 1, wherein the internal tube has an external diameter of between 3.6 and 5.7 cm and an internal diameter of between 0.3 and 0.7 cm.

9. The lysimeter device of claim 1, wherein, said sealing plate has a hole in said plate.

10. The lysimeter device is inserted into the external tube but does not touch sealing plate of claim 1, wherein, said internal tube reaches between 1.0 and 2.0 cm from said sealing plate.

11. The lysimeter device of claim 1, wherein, said opening is a longitudinal cut in said external tube having a longitudinal dimension of between 10 and 25 cm and a width between 2.0 and 8.0 cm.

12. The lysimeter device of claim 1, wherein, said opening in the wall of said external tube comprises more than one hole.

13. The lysimeter device of claim 1, wherein, said stabilizing-bar is a round tube.

14. The lysimeter device of claim 1, wherein, said stabilizing-bar has vertically protruding edge walls in its two edges.

15. The lysimeter device of claim 1, wherein, said geotechnical textile fabric component is produced from polypropylene material.

16. The lysimeter device of claim 1, wherein, said geotechnical textile fabric component is produced from polyester material.

17. The lysimeter device of claim 1, wherein, the diameter of the inert material beads is between 600 and 1,000 micrometer.

18. The lysimeter device of claim 1, wherein, said CPC is covered by a protection net made of a semi rigid material.

19. The lysimeter device of claim 18, wherein, more than one sensor are fixated in said external tube.

20. The lysimeter device of claim 1, wherein, a wire-connection or wireless connection sensor for agricultural soil content analysis is fixated in said external tube in the near of said sealing plate of said external tube.

* * * * *